(12) United States Patent
Cogan et al.

(10) Patent No.: US 9,439,625 B2
(45) Date of Patent: Sep. 13, 2016

(54) DELTA DELAY APPROACH FOR ULTRASOUND BEAMFORMING ON AN ASIC

(71) Applicant: General Electric Company, Schenectady, NY (US)

(72) Inventors: Scott D. Cogan, Clifton Park, NY (US); Lukas Bauer, Werder (DE)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 327 days.

(21) Appl. No.: 13/781,301

(22) Filed: Feb. 28, 2013

(65) Prior Publication Data

US 2014/0243676 A1    Aug. 28, 2014

(51) Int. Cl.
*A61B 8/00*     (2006.01)
*G10K 11/34*    (2006.01)

(52) U.S. Cl.
CPC ........... *A61B 8/4444* (2013.01); *G10K 11/346* (2013.01)

(58) Field of Classification Search
CPC ....... G01S 7/5202; A61B 8/00; A61B 8/483; B06B 1/0207; B06B 1/0607
USPC ................................ 600/459, 458, 447, 443
See application file for complete search history.

(56) References Cited

U.S. PATENT DOCUMENTS

| | | | |
|---|---|---|---|
| 5,891,038 A * | 4/1999 | Seyed-Bolorforosh et al. | 600/447 |
| 6,312,381 B1 | 11/2001 | Knell et al. | |
| 6,312,386 B1 | 11/2001 | Bolorforosh et al. | |
| 6,468,213 B1 | 10/2002 | Knell et al. | |
| 6,491,634 B1 | 12/2002 | Leavitt et al. | |
| 6,497,664 B1 | 12/2002 | Randall et al. | |
| 6,508,763 B1 | 1/2003 | Urbano et al. | |
| 6,561,979 B1 | 5/2003 | Wood et al. | |
| 6,595,921 B1 | 7/2003 | Urbano et al. | |
| 7,500,952 B1 * | 3/2009 | Chiang et al. | 600/446 |
| 7,678,048 B1 | 3/2010 | Urbano et al. | |
| 2002/0082502 A1 | 6/2002 | Urbano et al. | |
| 2004/0002656 A1 * | 1/2004 | Sheljaskow et al. | 600/459 |

(Continued)

FOREIGN PATENT DOCUMENTS

| | | |
|---|---|---|
| EP | 1744174 A1 | 1/2007 |
| WO | 2013024832 A1 | 2/2013 |

OTHER PUBLICATIONS

PCT International Search Report and Written Opinion from PCT Application No. PCT/US2014/019682 dated Jul. 14, 2014.

(Continued)

*Primary Examiner* — Baisakhi Roy
(74) *Attorney, Agent, or Firm* — Fletcher Yoder, P.C.

(57) ABSTRACT

Systems are disclosed for ultrasound beamforming on an application specific integrated circuit (ASIC). In certain embodiments, the system includes an ultrasound probe that includes a plurality of transducer elements electrically coupled to an ASIC. The ASIC includes a plurality of waveform generators electrically coupled to a plurality of delay units. Each delay unit receives a waveform from a waveform generator or an adjacent delay unit, applies a delay to the waveform, and outputs the waveform to adjacent delay units, one or more of the plurality of transducer elements, or both. The delays that are provided to waveforms before being output to a transducer element determine the beamforming characteristics of the ultrasonic pulses generated by the ultrasound probe.

24 Claims, 8 Drawing Sheets

(56) References Cited

U.S. PATENT DOCUMENTS

| | | |
|---|---|---|
| 2008/0221454 A1* | 9/2008 | Davidsen .................... 600/459 |
| 2008/0308343 A1 | 12/2008 | Vogt |
| 2009/0240152 A1 | 9/2009 | Angelsen et al. |
| 2011/0060225 A1* | 3/2011 | Cogan et al. ................ 600/459 |

OTHER PUBLICATIONS

John.V Hatfield, A beam forming transmit ASIC for driving ultrasonic arrays, Elesevier, Dec. 2000, Sensors and Actuators A 92 (2001) 273-279.

* cited by examiner

DELTA DELAY APPROACH FOR ULTRASOUND BEAMFORMING ON AN ASIC

BACKGROUND

The subject matter disclosed herein relates generally to ultrasound imaging, and more particularly, to application specific integrated circuits for use with beamforming assemblies for ultrasound imaging.

Medical diagnostic ultrasound is an imaging modality that employs ultrasound waves to probe the acoustic properties of the body of a patient and produce a corresponding image. Generation of sound wave pulses and detection of returning echoes is typically accomplished via a plurality of transducer elements located in the probe. Such transducer elements are capable of converting electrical energy into mechanical energy for transmission and mechanical energy back into electrical energy for receiving purposes. Some ultrasound probes include up to thousands of transducer elements arranged as linear arrays or a 2D matrix of elements.

Since the quality and resolution of a resulting image is largely a function of the size and number of transducer elements in such arrays, advanced systems typically incorporate the greatest number of transducer elements possible. However, since each transducer element typically is coupled to control circuitry, an increase in the number of transducer elements results in an associated increase in the complexity of the control circuitry.

BRIEF DESCRIPTION

In one embodiment, an ultrasound probe is provided. The ultrasound probe includes a plurality of transducer elements and an application specific integrated circuit (ASIC) coupled to the plurality of transducer elements. The ASIC also includes a plurality of delay units and a plurality of waveform generators each configured to generate and transmit waveforms with distinct parameters to at least one of the plurality of delay units. Each one of the plurality of delay units receives a waveform from a waveform generator or an adjacent delay unit, applies an additional delay to the waveform, and makes the delayed waveform available to adjacent delay units, one or more of the plurality of transducer elements, or both.

In a further embodiment, an ultrasound probe is provided. The ultrasound probe comprises a plurality of transducer elements and a plurality of delay units electrically coupled. Each of the plurality of delay units is configured to receive a waveform signal and output the waveform signal to one or more of the plurality of transducer elements as well as adjacent units of the plurality of delay units. The ultrasound probe also comprises a plurality of waveform generators configured to transmit the waveform signal to a subset of the plurality of delay units.

In another embodiment, a system is provided. The system includes a probe for use with an ultrasound system and an imaging system communicatively coupled to the probe via a bidirectional conduit. The probe comprises an array of transducer elements and one or more waveform generators configured to generate a plurality of delay differentiated waveforms. Additionally, the probe comprises a plurality of delay units configured to receive one of the plurality of delay differentiated waveforms, add a selectable incremental delay, and make a resulting delayed waveform available to adjacent delay units and the array of transducer elements.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

As discussed in further detail below, various embodiments of an ultrasound probe communicatively coupled to an imaging system are provided with respect to waveform generation proximate to the ultrasound probe. In one embodiment, the ultrasound probe is electronic, reusable, capable of precise waveform timing and intricate waveform shaping for a plurality of independent transducer elements, and capable of communicating analog or digitized data to the imaging system. The disclosed embodiments include a variety of probes that house one or more waveform generators on application specific integrated circuits (ASICs). The foregoing features, among others, may have the effect of reducing the size, complexity, and power consumption of an ASIC used in conjunction with an ultrasound array. The ASIC is sized and configured to work in a small space at relatively low power. However, the signal processing loads for the firing sequence of the ultrasound array and for the steering and/or focusing of the ultrasonic beam are relatively high.

In particular embodiments, an ultrasound array and its associated transmit and receive processing circuitry (i.e., the associated ASIC) may be implemented to be close to 1:1 in size such that the array of transmit/receive circuitry interconnects for each element on the ASIC may be directly coupled to the array itself. As the number of array elements increases, so does the complexity of the associated ASIC. While ultrasound probes may be implemented that include a dedicated waveform generator for each array element in the ultrasound array, such an arrangement involves a significant amount of circuitry for each element, and possibly complex routing of signals from the dedicated waveform generators from the periphery of the ASIC to the core of the array. Further, such an arrangement may be power intensive and space-constrained.

Provided herein are ultrasound probes and associated ASICs that incorporate delta delay techniques to address some or all of the above-mentioned issues. For example, in an ASIC as provided, delta delay circuit blocks receive a digitally-encoded waveform and make this waveform available to adjacent delta delay blocks. In certain embodiments, each delta delay block may add a selectable delay before passing the waveform on to adjacent blocks. Such delta delay blocks may be provided one per element, or group of elements present on the ASIC. In this manner, an ASIC may generate signals that determine the firing sequence of the subelements in the ultrasound array. Utilizing the firing sequence, the ASIC may steer and focus the ultrasonic beam to generate the desired beamforming shapes. The techniques disclosed herein incorporate delta delay blocks that propagate the waveform signals to the subelements of the ultrasound array with a reduced number of waveform generators. Reducing the number of waveform generators allows the ASIC to be less power intensive and allows the required circuitry to take up less space.

Figure 1:
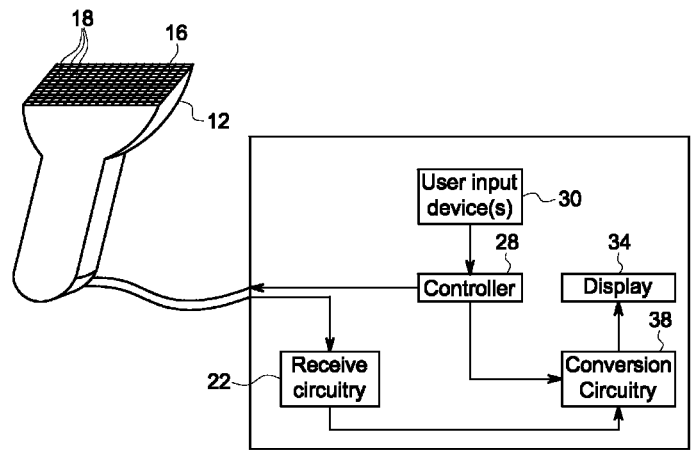
FIG. 1 illustrates an ultrasonic imaging system according to an embodiment of the disclosure.

As shown in FIG. 1, an ultrasonic imaging system 10 may include a variety of components, including a handheld probe 12 which contacts the patient during an ultrasound examination. In the depicted embodiment, the handheld probe 12 is in communication, such as via a wired or wireless communication link, with an ultrasound system or station 14 which controls operation of the probe 12 and/or processes data acquired via the probe 12.

In one embodiment, the probe 12 includes a patient facing or contacting surface that includes a transducer array 16 having a plurality of transducer elements 18 that are each capable of producing acoustic energy when energized by a pulsed waveform produced by waveform generators in an ASIC within the probe 12. The acoustic energy reflected back toward the transducer array 16, such as from the tissue of a patient, is converted to an electrical signal by the transducer elements 18 of the array 16, and the electrical signal is communicated to receive circuitry 22 of the station 14 for further processing to generate one or more ultrasound images. As will be appreciated, as used herein the term "circuitry" may describe hardware, software, firmware, or some combination of these which are configured or designed to provide the described functionality, such as transmit beamforming, receive beamforming, and/or scan conversion.

The receiver circuitry 22 is operated under control of a controller 28 that may operate in response to commands received from a human operator, such as via one or more user input devices 30 (e.g., a keyboard, touchscreen, mouse, buttons, switches, and so forth). Additionally, in certain embodiments, the controller 28 may send digital waveforms or control signals to the ASIC in the probe 12. In one embodiment, the controller 28 may be implemented as one or more processors, such as general-purpose or application-specific processors, in communication with other respective circuitry and/or components of the station 14.

In operation, an ultrasound scan is performed by using the probe 12 and station 14 to acquire a series of echoes generated in response to transmission of acoustic energy into the tissue of a patient. During such a scan, transducer elements 18 are energized to transmit acoustic energy. The acoustic energy may generate echo signals after reflecting off of structures or structure interfaces. The echo signals received by each transducer element 18 are communicated to the receive circuitry 22. The separate echo signals from each transducer element 18 are combined in the receive circuitry 22 into a signal which is used to produce a line in an image displayed on a display 34 incorporated in or in communication with the station 14.

In one embodiment, the transmit circuitry 20 may be configured to operate the transducer array 16 such that the acoustic energy emitted is directed, or steered, as a beam. For example, an ASIC within the probe 12 can impart respective time delays to generate temporally offset pulsed waveforms that are applied to respective transducer elements 18. These temporal offsets result in different activation times of the respective transducer elements 18 such that the wavefront of acoustic energy emitted by the transducer array 16 is effectively steered or directed in a particular direction with respect to the surface of the transducer array 16. Thus, by adjusting the time delays associated with the pulsed waveforms that energize the respective transducer elements 18, the ultrasonic beam can be directed toward or away from an axis associated with surface of the transducer array 16 by a specified angle ($\theta$) and focused at a fixed range, R, within the patient tissue. In such an implementation, a sector scan may be performed by progressively changing the time delays in successive excitations. The angle $\theta$ is thus incrementally changed to steer the transmitted beam in a succession of steering directions.

The echo signals produced by each burst of acoustic energy are reflected by structures or structure interfaces located at successive ranges along the ultrasonic beam. The echo signals are sensed separately by each transducer element 18 and a sample of the echo signal magnitude at a particular point in time represents the amount of reflection occurring at a specific range. However, due to the differences in the propagation paths between a reflecting structure and each transducer element 18, these echo signals may not be detected simultaneously. Therefore, in one embodiment, the receive circuitry 22 amplifies the separate echo signals, imparts the proper time delay to each, and sums them to provide a single echo signal which represents the total acoustic energy reflected from a point or structure located at range R along the ultrasonic beam oriented at the angle $\theta$.

To simultaneously sum the electrical signals produced by the echoes detected at each transducer element 18, time delays are introduced into the separate channels defined in the receive circuitry 22. In conventional ultrasound scans, the time delays for reception correspond to the time delays associated with transmission, described above, such that the receive beam has a corresponding steering direction as the transmit beam. That is, the steering direction from which acoustic energy is received generally corresponds to the steering direction in which the acoustic energy was transmitted. However, the time delay associated with each receive channel may be adjusted or changed during reception of the echo to provide some degree of dynamic focusing of the received beam at the range R from which the echo signal emanates. In embodiments of the present disclosure, as discussed herein, the delay profile employed for reception by the receive circuitry 22 may differ from the corresponding delay profile employed by the ASIC in the probe 12 such that the receive circuitry is effectively looking or scanning in a different direction from where the transmitted acoustic energy is directed, i.e., the steering direction of the receive beam differs from the steering direction of the transmit beam.

For example, of image data acquisition, the controller 28 provides the specified delays to the receive circuitry 22 to receive echo data along the direction θ, corresponding to the beam steered by the ASIC in the probe 12, and samples the echo signals at a succession of ranges R so as to provide the proper delays and phase shifts to dynamically focus at points P along the beam. Thus, each emission and reception of an ultrasonic pulse waveform during an image acquisition portion of an examination results in acquisition of a series of data points which represent the amount of reflected sound from a corresponding series of points P located along the ultrasonic beam.

In accordance with the present disclosure, acoustic noise data is also acquired during an examination. During acquisition of the acoustic noise signal, the controller 28 provides a different set of delays to the receive circuitry 22 to receive echo data from a direction other than θ, such that echo data is received from directions other than the direction of the transmitted ultrasound beam. Thus, each emission and reception of an ultrasonic pulse waveform during an acoustic noise measuring portion of an examination results in acquisition of a series of data points which represent the amount of reflected sound from directions other than that in which the ultrasound beam is directed.

Conversion circuitry 38 receives the various series of data points produced by the receive circuitry 22 and converts the data into the desired image and/or noise measurements. Alternatively, the controller 28 and/or other processor-based components of the station 14 may process the signals generated by the receive circuitry 22 that correspond to acoustic noise to generate measurements or other characterizations of the acoustic noise for display or for use by the conversion circuitry 38 in generating images.

In one embodiment, the conversion circuitry 38 converts the acoustic image data from polar coordinate (R-θ) sector format or Cartesian coordinate linear array to appropriately scaled Cartesian coordinate display pixel data suitable for display at a specified frame rate. This scan-converted acoustic data is then supplied to the display 34, which, in one embodiment, images the time-varying amplitude of the signal envelope as a grey scale.

Figure 2:
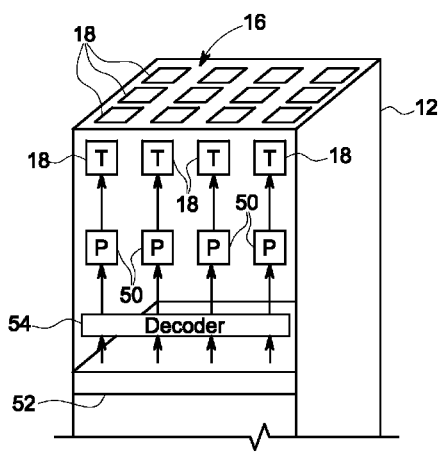
FIG. 2 illustrates the circuitry of the probe of the ultrasonic imaging system according to an embodiment of the disclosure.

FIG. 2 shows a schematic view of certain components of the handheld probe 12. The handheld probe 12 includes a patient-facing or contacting surface that includes the transducer array 16 having transducer elements 18 that are respectively capable of converting electrical energy to mechanical energy in ultrasound transmission and mechanical energy into electrical energy in an ultrasound receiving mode. In some embodiments, each transducer element 18 may include a piezoelectric ceramic, a matching layer, an acoustic absorber, and so forth. Additionally, the transducer elements 18 may be of any type suitable for use with diagnostic ultrasound, such as broad-bandwidth transducers, resonance transducers, and so forth. In certain embodiments, the transducer elements 18 may be voltage biased when receiving echoes back from the patient. That is, the transducer elements 18 may be precharged to a certain voltage (e.g., 1v, 2v) prior to receiving signals back from the patient such that all received signals take on a positive value. The foregoing feature may have the effect of simplifying electrical circuitry associated with the receiving cycle in certain embodiments.

In some embodiments, each transducer element 18 may be associated with a respective pulser 50 that receives a signal from a waveform delay circuit 52. For instance, a respective pulser 50 may receive control signals at a low voltage (e.g., 3.3V or 5.0V) and produce high voltage (e.g., negative 100V to positive 100V) signals that drive the transducer elements 18. The low voltage control signal may be a digitally encoded representation of the desired pulser state. Additionally, the pulser 50 having such functionality may receive a signal of a preset number of bits and generate a variety of independent signals from the information encoded in the received bits. For example, a signal of two bits may be decoded to generate four independent signals for four pulser states (e.g., high, low, ground, receive). It should be noted that any number of suitable bits may be encoded as the signal and any number of possible signals may be generated based on the number of received bits. In the illustrated embodiment, a decoder 54 may convert digital signals from the waveform delay circuit 52 to analog or digital control signals for the pulsers 50. In certain embodiments, each pulser 50 may include circuitry which may convert digital signals to analog signals.

The pulsers 50 may function as transmitters, which provide the voltage needed to excite the piezoelectric material (e.g., a ceramic) in the transducer elements 18. Accordingly, the pulsers 50 control the power transmitted to the patient via adjustment of an applied voltage. It should be noted that, in some embodiments, the ADC 54 may act in conjunction with the pulsers 50 or other elements contained in the handheld probe 12 to determine the amplitude of the applied voltage. In some embodiments, such as in a pulse echo operation mode, the pulsers 50 may pulse their respective transducer elements 18 at frequencies of several megahertz.

The present disclosure provides ASIC implementations that have increased flexibility but decreased complexity, particularly for 2D arrays of elements. As a result, the ASIC implementations of the present disclosure may require fewer waveform generators and related transmit beamforming circuitry to achieve the desired beamforming.

Figure 3:
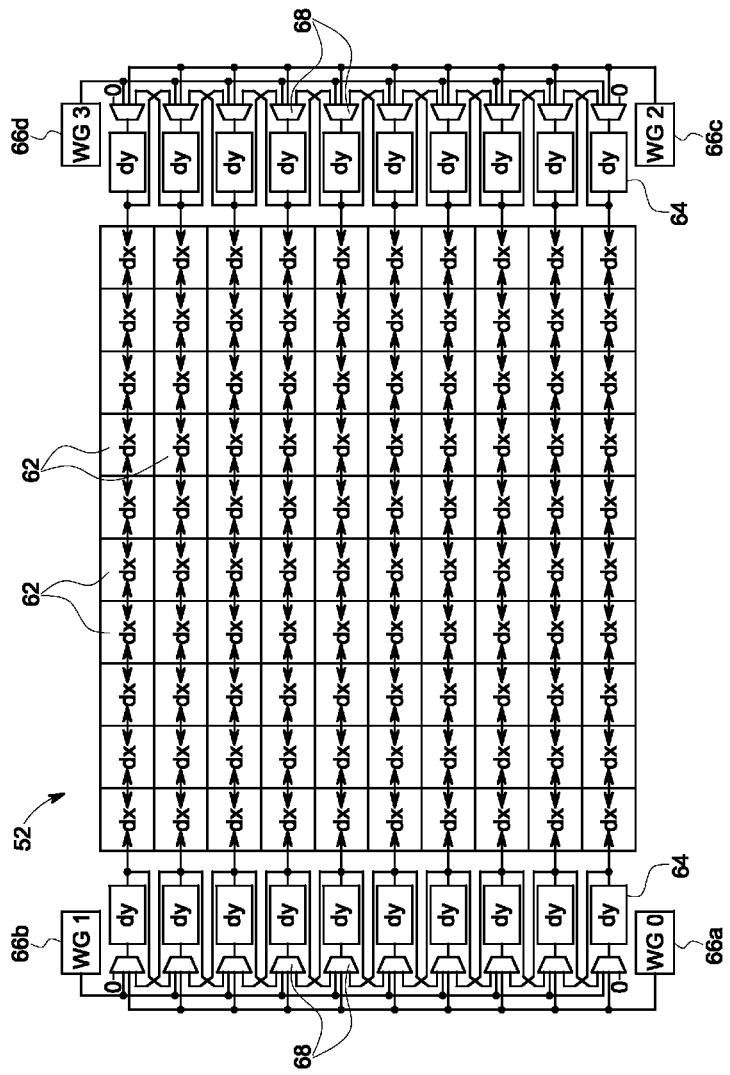
FIG. 3 illustrates a waveform delay circuit of the probe of the ultrasonic imaging system according to an embodiment of the disclosure.

In certain embodiments, the waveform delay circuit 52 provides signals to the pulsers 50 that are used to excite the transducer elements 18. To produce different ultrasound beam shapes, the waveform delay circuit may apply a series of delays to signals before they are output to the pulsers 50. FIG. 3 illustrates one example of a waveform delay circuit 52 that includes an array of $d_x$ delay units 62 that may include circuitry to electrically couple and provide signals to the pulsers 50. Additionally, columns of $d_y$ delay units 64 may be electrically coupled to rows of $d_x$ delay units 62. Each of the $d_x$ delay units 62 and the $d_y$ delay units 64 may receive a signal, introduce an incremental delay or no delay, and make the delayed signal available to adjacent blocks for subsequent delay and further distribution to other blocks and eventually, pulsers 50 and transducer elements 18. In some embodiments, each $d_x$ delay unit 62 may introduce a delay from 0 to 3 delay increments, where a delay increment is a function of a clock frequency of waveform generators of the waveform delay circuit 52. Similarly, in some embodiments, each $d_y$ delay unit 64 may introduce a delay from 0 to 7 delay increments. The resolution or fineness of the range of possible delay time depends on the arrangement and/or combination of circuitry disposed within each delay unit and the clock frequency with which the delay units are operated.

In the illustrated embodiment, to introduce signals, the waveform delay circuit 52 may include four waveform generators (WG0, WG1, WG2, and WG3) 66a-d that may generate delayed versions of a digitally-encoded waveform which may be sinusoidal and periodic. To determine which waveforms are supplied to each $d_y$ delay unit 64, 4-to-1 multiplexers 68 may receive input signals from two waveform generators 66 and the $d_y$ delay units 64 on either side of the multiplexer 68. Each multiplexer 68 may include a two bit selector input so a control system may determine which of the multiplexer inputs is passed to the corresponding $d_y$ delay unit 64. Each $d_y$ delay unit 64 applies a delay to the signal, and makes the signal available to the corresponding row of $d_x$ delay units 62 and adjacent $d_y$ delay units 64. In certain embodiments, the waveform generators 66a-d distribute the waveform signals along the $d_y$ delay units 64 on the periphery of the waveform delay circuit 52 in one dimension (Y), and subsequently distribute the waveform signals to the core of the element array with the $d_x$ delay units 62 in another dimension (X).

Each $d_x$ delay unit 62 receives a delayed signal, applies an additional delay, and outputs the signal to one or more pulsers 50 and adjacent $d_x$ delay units 62. Via delaying and passing a propagating signal throughout the waveform delay circuit 52, the control circuitry may achieve the desired shape and intensity of the acoustic waves being output by the transducer elements 18.

It should be noted that configurations of the waveform delay circuit 52 that differ from the implementation illustrated in FIG. 3 may also be implemented. For example, in FIG. 3, the waveform generators 66 are disposed on the periphery of the waveform delay circuit 52, but they may be disposed anywhere in the circuit as long as each waveform generator 66 is electrically coupled to at least one delay unit. Each waveform generator 66 does not necessarily provide a waveform signal to each of the delay units. In other words, in some embodiments, only a portion of the delay units receive a waveform from one of the waveform generators 66. Additionally, other embodiments may include more or less than four waveform generators 66, with the number of waveform generators 66 being directly related to power consumption and required silicon area, (i.e., the more waveform generators 66 that are present, the greater the power draw and the more silicon space required). The waveform delay circuit 52 is designed to allow the number of waveform generators 66 to be less than the number of delay units. For example, the ratio of waveform generators to delay units may be 1:5 or 1:20. Since each delay unit in connected to one or more transducer element 18, there are less waveform generators 66 than transducer elements 18 as well. In certain embodiments, the delay units may be arranged in other configurations other than an array. For example, the delay units may be arranged in concentric circles to form a circular probe 12. In other embodiments, the delay units may be arranged in a three-dimensional pattern to achieve more complex beamforming characteristics.

Figure 4:
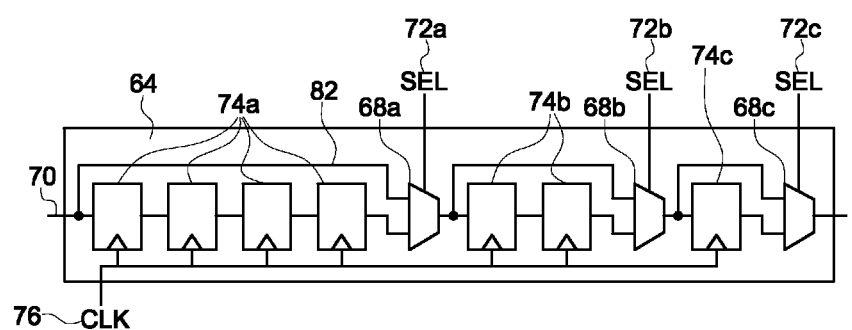
FIG. 4 illustrates a $d_y$ delay unit of the waveform delay circuit according to an embodiment of the disclosure.
Figure 5:
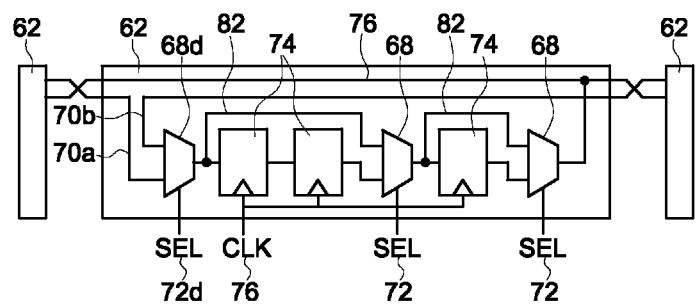
FIG. 5 illustrates a $d_x$ delay unit of the waveform delay circuit according to an embodiment of the disclosure.

As mentioned, each $d_x$ delay unit 62 and $d_y$ delay unit 64 includes circuitry to determine the delay applied to the signal propagating through the delay unit. FIG. 4 and FIG. 5 illustrate the delay circuitry of each $d_y$ delay unit 64 and each $d_x$ delay unit 62, respectively. The $d_y$ delay unit 64 of FIG. 4 may include an input line 70, and multiple 2-to-1 multiplexors 68a-c. The multiplexors 68a-c may receive a one-bit selection signal 72a-c to determine if the multiplexor 68 passes the waveform that has been delayed by a series of flip-flop circuits 74, or the waveform directed around the flip-flop circuits for no delay. It should be noted that the flip-flop circuits 74 are one possible implementation of a delay device. In other embodiments, other latches or sampling structures may replace the flip-flop circuits 74. For example, a selection signal 72 may be a digital "0" to select a signal with no delay, and may be a digital "1" to select a signal delayed by the preceding flip-flop circuits 74. However, it should be noted that even when a signal with no delay is selected (zero delay), each multiplexor 68 may still introduce a small delay (e.g. 2.5 nanoseconds). This inadvertent small delay may be referred to as a hardware propagation delay, while an intentional delay may be referred to as a selectable delay. For example, to form selectable delays, each flip-flop circuit 74 is designed to latch a value present on the input to the output based on the rising edge or falling edge of a clock signal 76. Therefore, a waveform propagating through a flip-flop circuit 74 will be delayed by one clock cycle in comparison to the same signal that did not propagate through the flip-flop 74. As illustrated, multiple flip-flop circuits 74 may be arranged in series to introduce delays for more than one clock cycle. Because each flip-flop circuit latches its input signal to its output on the falling edge or rising edge of the clock signal 76, the propagation delays introduced by the multiplexors 68 may be negated when the waveform signal passes through a flip-flop 74 if they are relatively small in comparison to the period of the clock signal 76. In this manner, a certain number of zero delays may be allowed until the hardware propagation delay is too large, such that the waveform is sampled by the next clock, resulting in an inadvertent extra delay from that point on.

In operation, a waveform may enter the delay unit 64 on the input line 70 and propagate through the first series of flip-flop circuits 74a and the corresponding parallel wire 82. The selection signal 72a may be a digital "0", causing the multiplexor 68a to pass the waveform from the parallel wire 82, with no delay. As before, the waveform may then propagate through the second series of flip-flop circuits 74b and the corresponding parallel wire 84. The selection signal 72b may be a digital "1", causing the multiplexor 68b to pass the waveform that has been delayed by the series of flip-flop circuits 74b. Finally, the waveform may propagate through the last flip-flop circuit 74c and the corresponding parallel wire 86. The selection signal 72c may be a digital "0", introducing no further delay to the final waveform output to an output line 88. In this manner, a $d_y$ delay unit 64 such as the embodiment illustrated in FIG. 4 may delay a waveform by a time approximately equal to the latency of two flip-flop circuits 74, or two clock cycles. With other selection signal 72 configurations, a $d_y$ delay unit 64 as illustrated in FIG. 4 may delay a waveform by a configurable number of clock cycles, between 0 and 7. It should be appreciated that in other embodiments, additional series of multiplexors 68 and flip-flop circuits 74 may be added to increase the possible maximum delay of the $d_y$ delay unit 64.

The $d_x$ delay unit 62 of FIG. 5 may operate in a similar manner to the $d_y$ delay unit 64 illustrated in FIG. 4. As before, the $d_x$ delay unit 62 may include multiplexors 68 with selection signals 72 to force the waveform to be delayed by one or more flip-flop circuits 74 or has no delay. An additional multiplexor 68d with corresponding selection signal 72*d*, may select which input line 70*a*, 70*b* from adjacent $d_x$ delay units 62 will provide the waveform to the delay unit 62. After propagating through series of multiplexors 68 and flip-flop circuits 74, the waveform is output to the output line 78 that feeds to both adjacent $d_x$ delay units 62.

Figure 6:
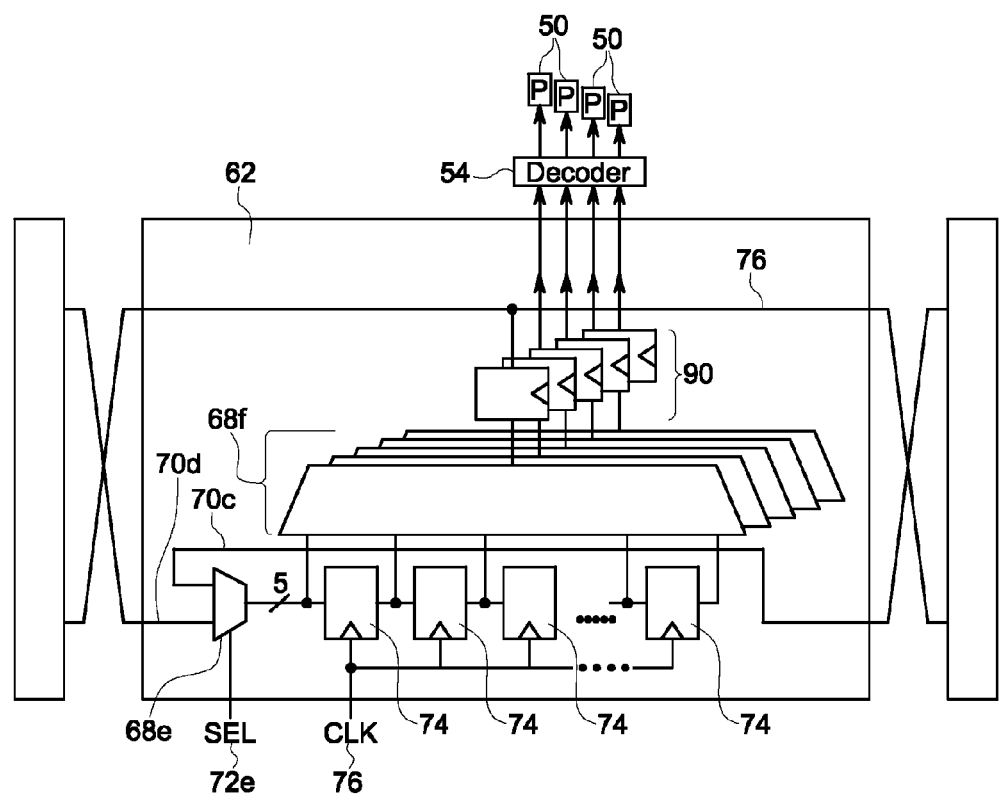
FIG. 6 illustrates a $d_x$ delay unit of the waveform delay circuit according to an embodiment of the disclosure.

It should be noted that other embodiments of the $d_y$ delay unit 64 of FIG. 4 and the $d_x$ delay unit 62 of FIG. 5 may have different configurations that the illustrated embodiments. For example, in the $d_x$ delay unit 62 of FIG. 5, a multiplexor 68*d* is included within the $d_x$ delay unit 62 to select the input to the $d_x$ delay unit 62. While the illustrated $d_y$ delay unit 64 of FIG. 4 does not include the input selection multiplexor, other embodiments of the $d_y$ delay unit 64 may include an input selection multiplexor. Likewise, in other embodiments, the input selection multiplexor 68*d* of the $d_x$ delay unit 62 may be external to the delay unit circuitry. FIG. 6 illustrates an alternative embodiment of the $d_x$ delay unit 62 illustrated in FIG. 5. As before, the $d_x$ delay unit 62 includes a multiplexor 68*e* that may receive a selection signal 72*e* to determine the input line 70*c*, 70*d* that will provide the waveform to the $d_x$ delay unit 62. In the embodiment illustrated in FIG. 6, the waveform may be represented by 5 bits. In other embodiments, the waveform signal may be represented by more or less bits. A greater number of bits may increase the precision of the waveform signal, allowing for more precise control of the pulsers 50 and transducer elements 18. By way of example, 5 bits may offer 32 distinguishable levels of the waveform.

As illustrated, the $d_x$ delay unit 62 of FIG. 6 includes multiple series of 15 flip-flop circuits 74 each feeding outputs to a series of 16-to-1 multiplexors 68*f*, where these is one multiplexor for each pulser 50 associated with the delay unit, and one multiplexor for choosing the delayed waveform to pass to adjacent delay units. Although more complex, the $d_x$ delay unit 62 of FIG. 6 may enable precise control of delays applied to waveforms being passed through the delay unit. Additionally, the $d_x$ delay unit 62 of FIG. 6 may be able to provide waveforms with a variety of delays to a plurality of pulsers 50 and transducer elements 18. In operation, each 16-to-1 multiplexor 68*f* may receive a 4-bit selection signal which may determine which flip-flop circuit 74 output may be passed through the multiplexor 68*f*, effectively determining the amount of delay that will be applied to each waveform propagating through the $d_x$ delay unit 62 to the pulsers 50. For example, a selection signal to a multiplexor 68*f* may be a digital "0110", meaning that the output from the sixth flip-flop circuit 74 may be passed through the multiplexor 68*f*. In this case, the output signal from the multiplexor may be delayed by a value approximately equal to the latency of six flip-flop circuits 74, or 6 clock cycles. One of the 16 multiplexors 68*f* may feed the waveform signal through a local sync flip-flop circuit 90 and to an output line 76 that electrically couples to adjacent $d_x$ delay units 62. The other 15 multiplexors 68*f*, may also feed their corresponding waveform signals through a local sync flip-flop circuit 90 to a decoder 54 to be converted from a digital representation of the waveform signal to a digital or analog control signal. The digital or analog control signals may be supplied to a respective pulser 50 to have the voltage amplified before being sent to a transducer element 18. The local sync flip-flop circuits 90 may serve to synchronize the propagating waveforms with one another since flip-flop circuits 74 latch the signal present on their input to their output on the rising or falling edge of a clock signal. Because the different waveforms may be purposefully delayed from one another, the local sync flip-flop 90 simply negates any unintentional delays such as circuit or multiplexor 68 latency, ensuring that the delayed waveforms are precisely delayed from one another by the correct amount. It should be noted that the $d_y$ delay unit 64 shown in FIG. 4 and the $d_x$ delay units 62 shown in FIGS. 5 and 6 are only possible embodiments of delay units, and other embodiments may be used.

Even when no delay is intended, each multiplexor 68 may inherently introduce a small amount of delay to waveform signals propagating through the multiplexor 68. But, because the flip-flop circuits 74 latch a signal present on their input to their output based on the rising edge or falling edge of the clock signal, the small delays caused by the multiplexor may be cancelled each time the signal propagates through a flip-flop circuit 74. However, if a waveform signal propagates through enough multiplexors 68 without being corrected by passing through a flip-flop circuit 74, the accumulated delay may actually be long enough to delay the waveform signal by a clock period.

Figure 7:
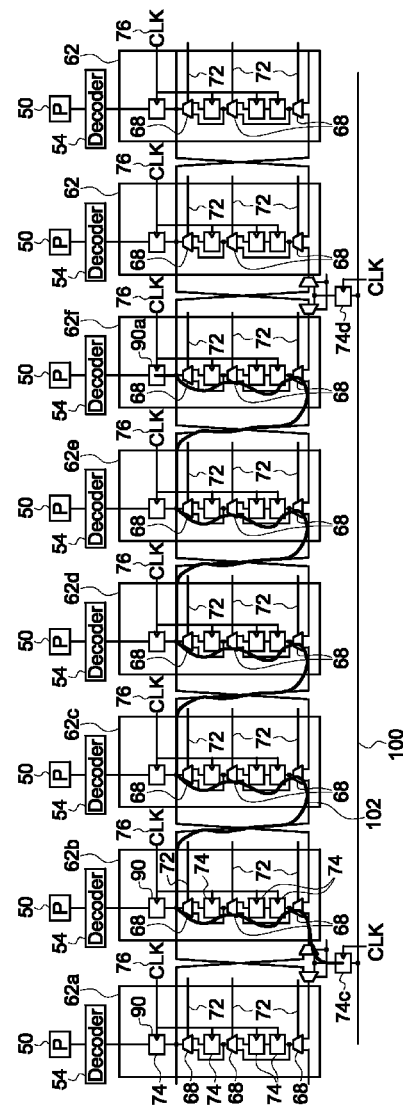
FIG. 7 illustrates a series of $d_x$ delay units with a global waveform input line according to an embodiment of the disclosure.

FIG. 7 illustrates a series of $d_x$ delay units 62 electrically coupled to a global waveform input line 100 to provide a synchronized waveform signal to the delay units 62, preventing delay caused by the multiplexors 68. The data flow line 102 illustrates a possible propagation path of a waveform if a series of $d_x$ delay units 62 need to output waveform signals with no delay shift. The waveform signal must propagate through 15 multiplexors 68 before reaching the local sync flip-flop circuit 90*a*. In this case, the delays to the waveform signal caused by each of the multiplexors 68 may accumulate to delay the waveform signal into a later clock cycle. For example, the delay caused by each multiplexor 68 may be 15 nanoseconds. After 15 multiplexors 68 the waveform signals may be delayed by 225 nanoseconds. If the clock is operating at 5 MHz, the period of the clock signal is 200 nanoseconds, meaning that the waveform signal may be delayed a clock cycle as it is latched to the output of the local sync flip-flop circuit 90*a* in comparison to the signals latched to the outputs of the other local sync flip-flop circuits 90*b-e*.

However, in the illustrated embodiment, the global waveform input line 100 may provide a synchronized waveform signal to alleviate multiplexor 68 delay issues. For example, $d_x$ delay units 62*a-c* may receive the waveform signal from a nearby flip-flop circuit 74*c* electrically coupled to the global waveform input line 100. Likewise, $d_x$ delay units 62*d-f* may receive the waveform signal form a nearby flip-flop circuit 74*d* electrically coupled to the same global waveform input line 100. In this manner, the waveform signals may not propagate though enough multiplexors 68 to become de-synchronized. In certain embodiments, the global waveform input line 100 may extend from a $d_y$ delay unit 64 as shown in FIG. 3 to supply the synchronized waveform signal to its corresponding row of $d_x$ delay units 62.

Figure 8:
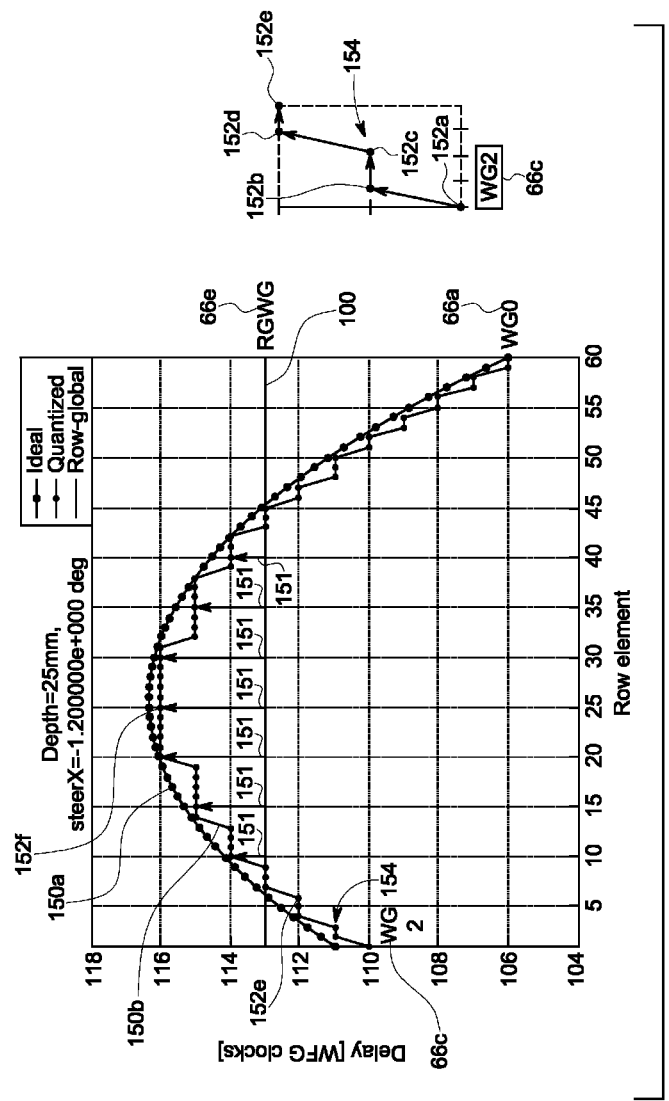
FIG. 8 illustrates a graph of a delay curve that may allow beamforming of ultrasonic pulses generated by pulsers on the application-specific integrated circuit according to an embodiment of the disclosure.

The embodiments provided herein are examples of ASIC implementations that introduce delays to the transducer array 16 to determine the firing sequence of the transducer array 16. It should be understood that other arrangements of the delta delay units, waveform generators 66, and multiplexors 68 that facilitate waveform generation are also contemplated. In turn, the firing sequence may determine the beamforming characteristics, such as steering and focusing, of the ultrasonic beam generated by the transducer array 16. The graph of FIG. 8 illustrates the relationship between the waveform generators 66, incremental delays, and the final delay of the waveform being output to each element of the transducer array 16. The x-axis 146 of the graph refers to an element of a row of the transducer array 16, and the y-axis 148 refers to a delay (in clocks) that is ultimately applied to a given element of a row of the transducer array 16.

The graph of FIG. 8 illustrates two delay curves 150a-b that represent the number of clock cycles of delay that a given element of a row of the transducer array 16 may require for a particular beamform shape. It should be noted that the clock cycle values on the x-axis of the graph of FIG. 8 may be approximate. Delay curve 150a illustrates the ideal delay curve required for a particular beamform shape, while delay curve 150b illustrates the actual delays achievable, quantized to the resolution of a single clock cycle, which can reasonably be generated by the delay circuitry. The number of delay units in a given row and the range of delay times that each delay unit can determine the accuracy of the quantized delay curve 150b in comparison to the ideal delay curve 150a. That is, a greater number of delay units and a finer control of delay times may make the quantized delay curve 150b more accurate in comparison to the ideal delay curve 150a.

As illustrated, certain elements may source their signal from WG2 66c, the row global waveform generator 66e, or WG0 66a. For example, in the depicted embodiment showing 60 elements, the first 10 elements are sourced from WG2 66c while the rightmost 20 elements are sourced from WG0 66a. The middle 10-40 elements illustrate a case in which the signal for certain portions of the curve may be sourced from the RGWG 66e. In such an embodiment, it may be advantageous to avoid hardware-associated delays by sourcing the signal every five elements directly from the RGWG 66e, as represented by arrows 151. The arrows 151 indicate injection points of the row-global waveform generator 66e into the array. It should be understood that, in particular embodiments, the row global injection points may be spaced differently based on the particular embodiment and may be, for example, every 3 elements, every 7 elements, or none at all.

As shown in detail view, the five elements in graph segment 154 are illustrated in more detail. The first element, represented by point 152a, may receive the waveform signal from waveform generator WG2 66c and apply a delay of 1 clock cycle before outputting the signal to its corresponding pulser 50 and transducer element 18. The second element, represented by point 152b, may then receive the delayed waveform from the first element and apply no delay before outputting the signal to the corresponding pulser 50 and transducer element 18. In the same way, the third element, represented by point 152c, may receive the delayed waveform and delay an additional 1 clock cycle, the fourth element, represented by 152d, may receive the delayed waveform and apply no delay, and finally, the fifth element, represented by point 152e may receive the delayed waveform and apply no delay since the waveform is already delayed by the desired 112 clock cycles. In this way, the correct delays are applied to transmitted waveforms output by the delay units corresponding to the elements of the transducer array 16. It should be noted that the delays and delay resolution may be described in terms of a phase delay at a particular frequency rather than in clock cycles. For example, in a certain embodiment, each clock cycle may be equivalent to 45° of phase delay at the TX center frequency.

In the illustrated graph, the waveform signal of point 152e described above originated from waveform generator WG2 66c. However, some of the points of the delay curves 150 may be ultimately sourced from a different waveform generator 66, possibly through one or more adjacent delay units. For example, point 152f may either be sourced from waveform generator WG2 66c in the same method mentioned above, or it may be sourced from a row-global waveform generator RGWG 66e. As shown in FIG. 7, the row-global waveform generator 66e may electrically couple to a global waveform input line 100 to provide a single delayed waveform to delay elements in a given row So the fifteenth element of a row of the transducer array 16, as represented by point 152f, may receive the waveform signal directly from the global waveform input line 100 and apply the necessary delay (in this example, 3 clock cycles) to output the waveform signal with the necessary delay.

In another embodiment, element delay profiles may be achieved by combining a bulk delay and a fine delay. FIGS. 9-12 illustrate different delay curves 150 and their corresponding bulk and fine delays that may be necessary to generate different beamforming shapes. In some embodiments, the bulk delay is associated with the signal that propagates through the delta-delay circuitry, and is passed to adjacent delay units which correspond to a plurality of elements, while the fine-delay adds a smaller delay on a per-element basis. In other words, a plurality of elements may share the same bulk delayed waveform input, and each element may add a small fine delay profile on top of this.

Figure 9:
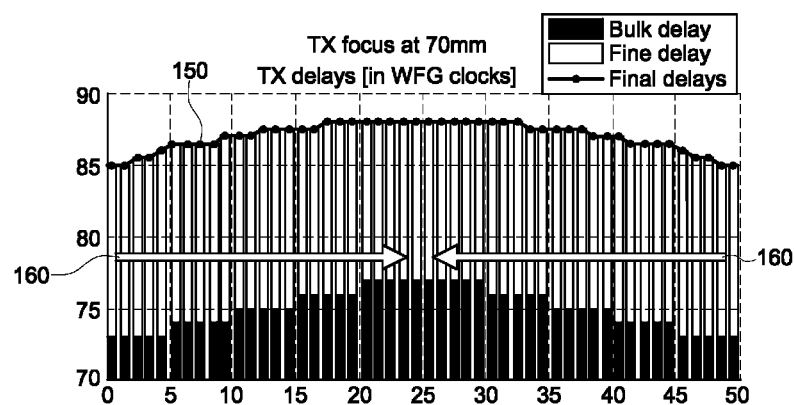
FIG. 9 illustrates a graph of a delay curve that may allow beamforming of ultrasonic pulses generated by the ultrasonic imaging system and the corresponding bulk delays and fine delays that form the delay curve according to an embodiment of the disclosure.

For example, in FIG. 9, propagation arrows 160 start from the edges and proceed toward the center of the graph and the bulk delay increases accordingly. In FIGS. 9-12, a delay unit may apply to multiple elements, such as illustrated in FIG. 6. In the embodiments illustrated by FIGS. 9-12, each delay unit corresponds to five elements. In the illustrated embodiments, a waveform generator 66 supplies a waveform to a first delay unit that includes elements 1-5 and a different waveform generator 66 supplies a waveform to a tenth delay unit that includes elements 46-50. The first delay unit passes its waveform to a second element that includes elements 6-10, and the tenth delay unit passes its waveform to a ninth delay unit that includes elements 41-45, and so on. At each element, the delay unit may apply a fine delay that may be added to the bulk delay received by the delay unit to achieve the desired final delay.

Figure 10:
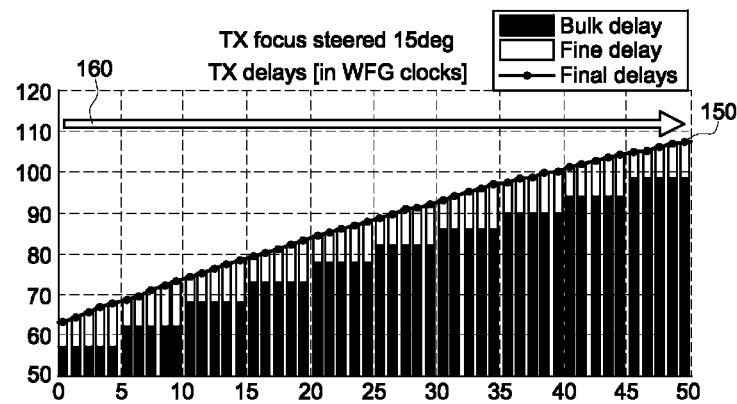
FIG. 10 illustrates a graph of a delay curve that may allow beamforming of ultrasonic pulses generated by the ultrasonic imaging system and the corresponding bulk delays and fine delays that form the delay curve according to an embodiment of the disclosure.
Figure 11:
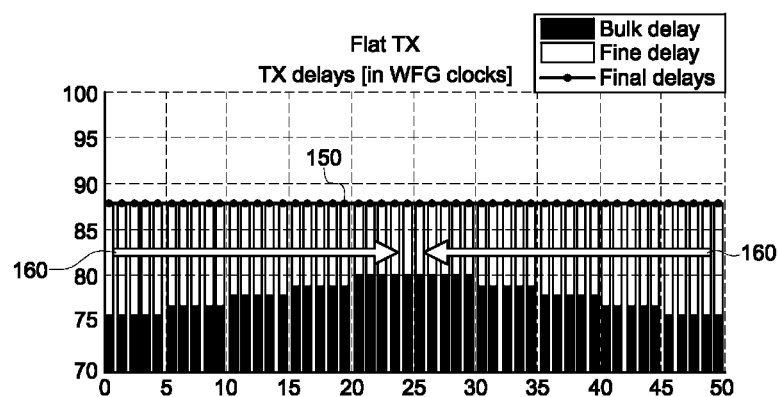
FIG. 11 illustrates a graph of a delay curve that may allow beamforming of ultrasonic pulses generated by the ultrasonic imaging system and the corresponding bulk delays and fine delays that form the delay curve according to an embodiment of the disclosure.
Figure 12:
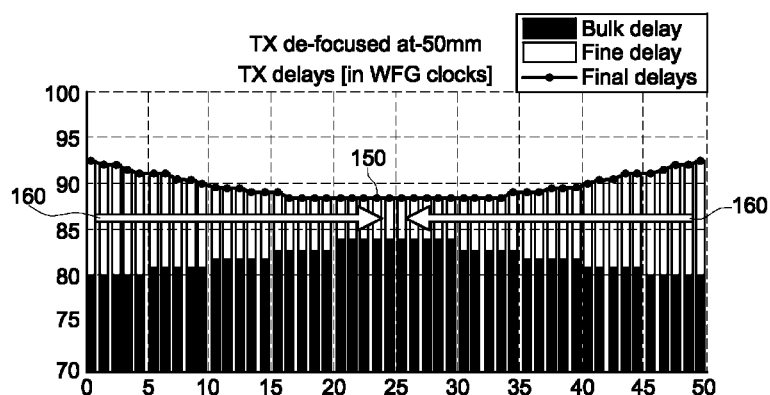
FIG. 12 illustrates a graph of a delay curve that may allow beamforming of ultrasonic pulses generated by the ultrasonic imaging system and the corresponding bulk delays and fine delays that form the delay curve according to an embodiment of the disclosure.

In contrast to FIG. 9, FIG. 10 illustrates a case where a single propagation arrow 160 proceeds from left to right across the graph, corresponding to a situation where a waveform generator 66 supplies a waveform to a first delay unit that includes elements 1-5 and the first delay unit incrementally passes the waveform subsequent delay units that include each of the elements 6-50. The shape of the bulk delays is intentionally matched as closely as possible to the final delay curve 150, to allow for relatively small fine delays to match the desired overall delay profile. Based on the shape of the final delay curve 150, different combinations of waveform generators may be used as sources for the delay units. The graphs in FIG. 11 and FIG. 12 illustrate other embodiments of final delay curves and corresponding bulk and center delays.

Technical effects of the disclosure include a waveform delay circuit that includes waveform generators and an array of delay unit circuits. In order to generate beamforming signals for the operation of an ultrasound system, each delay unit circuit receives a waveform signal from either a waveform generator or another delay unit circuit, adds an incremental delay, and makes this delayed signal available to adjacent blocks for subsequent delay and further distribution. In this way, the signals propagate through the array of delay unit circuits with the appropriate delays for generating specific beamforming shapes when output through the pulsers and a transducer elements.

This written description uses examples to disclose the present approach, including the best mode, and also to enable any person skilled in the art to practice the present approach, including making and using any devices or systems and performing any incorporated methods. The patentable scope of the present approach is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound probe, comprising:
   a plurality of transducer elements; and
   an application specific integrated circuit (ASIC) coupled to the plurality of transducer elements, wherein the ASIC comprises:
   a plurality of delay units;
   one or more waveform generators configured to generate and transmit a waveform with distinct parameters to at least one of the plurality of delay units, wherein the at least one delay unit receives the waveform from one of the plurality of waveform generators or an adjacent delay unit, applies a delay to the waveform, and outputs a delayed waveform to an adjacent delay unit; and
   a plurality of multiplexors configured to control passing of the waveform from the waveform generators to the plurality of delay units; and
   wherein one or more delay unit of the plurality of delay units is configured to output the waveform signal to one or more of the plurality of transducer elements.

2. The ultrasound probe of claim 1, wherein the distinct parameters comprise one or more of waveform shape or waveform timing delay.

3. The ultrasound probe of claim 1, wherein the delay units utilize flip-flop circuits to apply the delay to the waveform.

4. The ultrasound probe of claim 1, wherein the delay units apply a selectable delay to the waveform.

5. The ultrasound probe of claim 1, wherein the delay units apply a hardware-associated delay to the waveform.

6. The ultrasound probe of claim 1, wherein a subset of the plurality of delay units is capable of receiving the waveform from more than one waveform generator.

7. The ultrasound probe of claim 1, wherein the plurality of delay units comprises at least one column of delay units on the periphery of the ASIC, and wherein respective individual delay units are configured to provide the waveform to a corresponding row of delay units.

8. The ultrasound probe of claim 1, wherein the plurality of waveform generators is directly electrically coupled to a subset of delay units on the periphery of the ASIC.

9. The ultrasound probe of claim 1, wherein at least one delay unit distributes the delayed waveforms in a first dimension on the periphery of the ASIC and subsequently distributes the waveforms in a second dimension.

10. The ultrasound probe of claim 1, wherein the number of waveform generators is less than the number of delay units.

11. The ultrasound probe of claim 1, wherein the ratio of waveform generators to delay units is less than 1:5.

12. The ultrasound probe of claim 1, wherein the ratio of waveform generators to delay units is less than 1:20.

13. The ultrasound probe of claim 1, wherein only a portion of the delay units receive the delayed waveform from one of the plurality of waveform generators.

14. The ultrasound probe of claim 1, wherein the delay units make delayed waveforms available to one or more of the plurality of transducer elements.

15. The ultrasound probe of claim 1, wherein plurality of transducer elements comprises a 2D array.

16. The ultrasound probe of claim 1, wherein the delay units comprise an array of delay units.

17. The ultrasound probe of claim 16, wherein each delay unit of the array of delay units comprises a local sync flip-flop to remove a hardware-associated delay from the waveform.

18. The ultrasound probe of claim 16, wherein a global waveform input line extends to multiple delay units on one or more rows of the array of delay units, one or more columns of the array of delay units, or a combination thereof.

19. The ultrasound probe of claim 16, wherein at least one of the plurality of delay units is coupled to a plurality of adjacent delay units.

20. An ultrasound probe, comprising:
    a plurality of transducer elements; and
    a transmit circuitry coupled to the plurality of transducer elements to energize the plurality of transducer elements to transmit acoustic energy, comprising:
    a plurality of delay units electrically coupled to one or more of the plurality of transducer elements and wherein one or more delay units of the plurality of delay units are configured to receive a waveform signal and output the waveform signal to one or more of the plurality of transducer elements and to at least one adjacent delay unit;
    a plurality of waveform generators configured to transmit the waveform signal to one or more delay units of the plurality of delay units; and
    a plurality of multiplexors configured to control passing of the waveform from the waveform generators to the plurality of delay units.

21. The ultrasound probe of claim 20, wherein the waveform signal comprises parameters defining a waveform shape or waveform timing delay.

22. The ultrasound probe of claim 21, wherein the timing delay ranges from 0° to 135°.

23. The ultrasound probe of claim 21, wherein at least a portion of the plurality of delay units apply a selectable delay to the waveform signal before the waveform signal is output to the at least one adjacent delay unit.

24. The ultrasound probe of claim 23, wherein the delay units utilize one or more series of one or more flip-flop circuits to apply the selectable delay to the waveform signal.

* * * * *